United States Patent [19]

Kurz

[11] Patent Number: 5,097,713
[45] Date of Patent: Mar. 24, 1992

[54] APPARATUS FOR TESTING THE STIFFNESS OF FABRICS

[76] Inventor: Milton Kurz, Pond Crossing, Lawrence, N.Y. 11559

[21] Appl. No.: 639,128

[22] Filed: Jan. 9, 1991

[51] Int. Cl.⁵ ............................................. G01N 3/20
[52] U.S. Cl. .............................................. 73/849
[58] Field of Search ............... 73/849, 854, 159, 431

[56] References Cited

U.S. PATENT DOCUMENTS

| | | | |
|---|---|---|---|
| D. 119,743 | 4/1940 | Dreyfuss | 73/431 |
| 3,057,191 | 10/1962 | Holloway | 73/849 |
| 3,368,394 | 2/1968 | Pasinski et al. | 73/854 |

FOREIGN PATENT DOCUMENTS

| | | | |
|---|---|---|---|
| 1114356 | 4/1956 | France | 73/849 |
| 0028639 | 2/1987 | Japan | 73/849 |
| 8907267 | 8/1989 | World Int. Prop. O. | 73/849 |

OTHER PUBLICATIONS

ASTM Designation D-1388-64.
ASTM Designation D-4032-82.
Hosiery Times, Mar. 1953, pp. 59 and 61.
Japan Textile News, Sep. 1976, p. 107.
Kettenwirk-praxis Apr. 1973, pp. 17–18.
Thwing-Albert Handle-O-Meter.
Textile Month, Aug. 1988, p. 77.
Textile Industries, Jan. 1968, pp. 86, 85, 91, 92, 94.
Advertisement J. A. King, Air Operated Fabric Stiffness Tester.
Advertisement J. A. King Fabric Stiffness Tester.
British Knitting Industry, Apr., 191, p. 62.
Textile Industries, May 1954, p. 118.

*Primary Examiner*—Robert Raevis
*Attorney, Agent, or Firm*—Brumbaugh, Graves, Donohue & Raymond

[57] ABSTRACT

Apparatus for testing the stiffness of fabrics comprises a box defining a space that is free of air currents, the top wall being movable to permit access to the space, the rear wall having a planar inside surface and the front wall being planar and parallel to the inside surface of the rear wall and being transparent to enable the space and the inside of the rear wall to be viewed from outside the box. A shelf mounted within the space and having a planar top surface bounded by a straight edge that is aligned substantially perpendicularly to the front wall supports a portion of a fabric sample. The remainder of the sample drapes freely from the edge of the shelf. A plate is placed on the portion of the sample on the shelf to hold it flat and stationary. Indicia marked on the inside face of a mirror on the rear wall of the box indicate the amount of drape of the portion of the fabric draping from the edge of the shelf. The mirror enables a viewer to view the indicia from a vantage point in which the indicia and the reflection of the indicia are aligned, thereby eliminating parallax and improving the accuracy of the measurement.

3 Claims, 1 Drawing Sheet

APPARATUS FOR TESTING THE STIFFNESS OF FABRICS

BACKGROUND OF THE INVENTION

It is often desirable and sometimes important to be able to determine the stiffness of a fabric, inasmuch as stiffness affects the properties of a finished product made from the fabric or the performance of the manufacturing process by which the finished product is made. Previously known testers have not been suitable for accurately determining the stiffness of light weight fabrics. In one known stiffness tester that has been used for light weight fabrics a sample is slid off a plane, and the angle of the fall is measured. Static electricity causes variations in the angle of fall, which makes this type of tester very unreliable.

SUMMARY OF THE INVENTION

One object of the present invention is to provide an apparatus for testing the stiffness of fabrics that provides highly reliable results and is not influenced by static electricity, air currents and other environmental conditions. Another object is to provide a stiffness tester that can be used for testing not only light-weight fabrics but heavier weight fabrics as well. Still another object is to provide a fabric stiffness tester that is of simple construction and that can, therefore, be produced economically. It is also desired to provide a stiffness tester that is easy to use.

The foregoing objects are attained, according to the present invention, by a fabric stiffness tester comprising a box having top, bottom, front, rear and left and right side walls defining a space that is free of air currents, the top wall being movable to permit access to the space. The rear wall has a planar inside surface, and the front wall is planar and parallel to the inside surface of the rear wall and is transparent to enable the space and the inside of the rear wall to be viewed from outside the box. A shelf is mounted within the space. The shelf has a planar top surface bounded by a straight edge that is aligned substantially perpendicularly to the front wall and is adapted to support a portion of a fabric sample with the remainder of the sample draping freely from the straight edge. A plate is provided for holding the portion of the sample on the shelf flat and stationary. Indicia are marked on the inside of the rear wall of the box to indicate the amount of drape of the portion of the fabric draping from the edge of the shelf.

In a preferred embodiment the inside of the rear wall is the surface of a mirror. The mirror has a planar rear surface that is parallel to and spaced apart from the inside surface and has a reflective layer so that the indicia are reflected and the indicia and the reflection of the indicia may be aligned by a viewer to eliminate parallax when the test is being conducted. Preferably, the top wall of the box is transparent to admit light to facilitate viewing the sample and the indicia. The indicia may consist of straight lines extending radially in diverse directions with respect to a point where a line defined by the straight edge of the shelf intersects the inside surface of the rear wall and different characters for distinctly identifying each line.

Using the tester is extremely simple. The operator opens the top, places the fabric sample, which is of a predetermined size and shape, on the shelf with a predetermined portion resting on the shelf and the remainder draping from the edge and places the plate on the portion of the sample on the shelf to hold it flat and stationary. The top is replaced to close the box. The operator then views the sample through the transparent front wall against the indicia on the rear wall and observes and records the indication of where the free edge of the sample resides. The operator positions his or her eyes at a point where the particular indicia being read is aligned with the image of that indicia, thereby eliminating parallax that would otherwise influence the reading.

The test is designed to provide reliable and repeatable indications of the stiffnesses of samples of a particular fabric type to ensure that different runs of the fabric have a desired stiffness rather than to provide absolute values of stiffness of different fabric types. The test can, however, be used for different fabric types over a broad range of weights and stiffnesses. If necessary, the sizes and shapes of the test samples can be varied with different fabric types to optimize the accuracy of the test. For example, the sizes of the test samples of stiffer fabrics may be made larger (wider, longer, or both wider and longer) than those of less stiff fabrics to increase the drape to the mid-range of the indicia.

For a better understanding of the invention, reference may be made to the following description of an exemplary embodiment, taken in conjunction with the accompanying drawings.

DESCRIPTION OF THE EMBODIMENT

Figure 1:
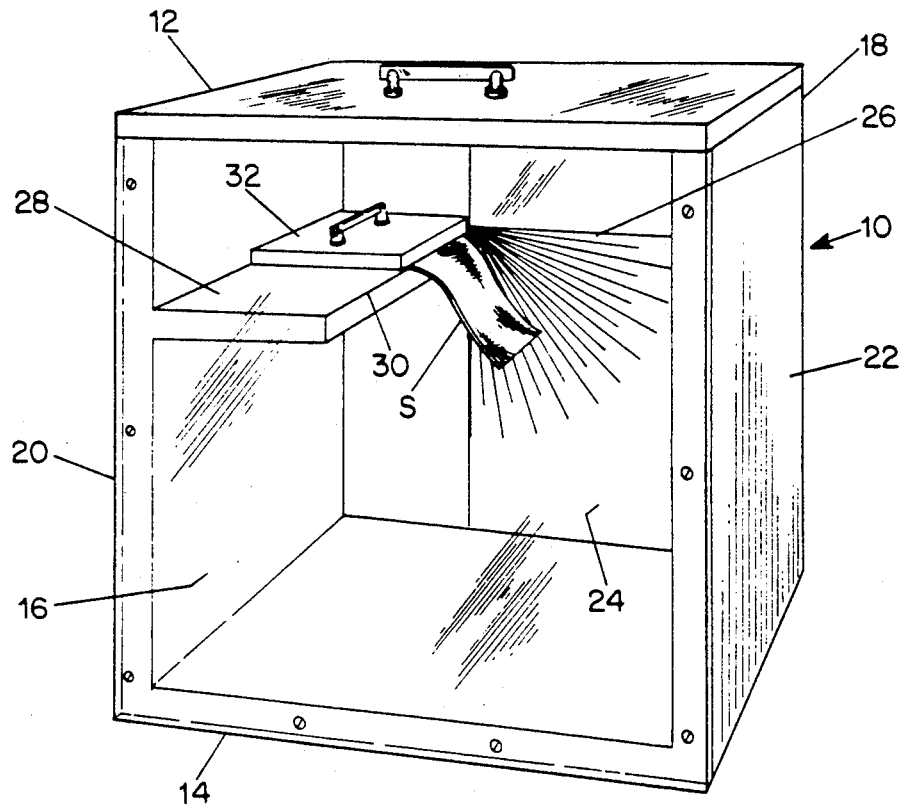
FIG. 1 is a front three-quarter pictorial view of the embodiment.
Figure 2:
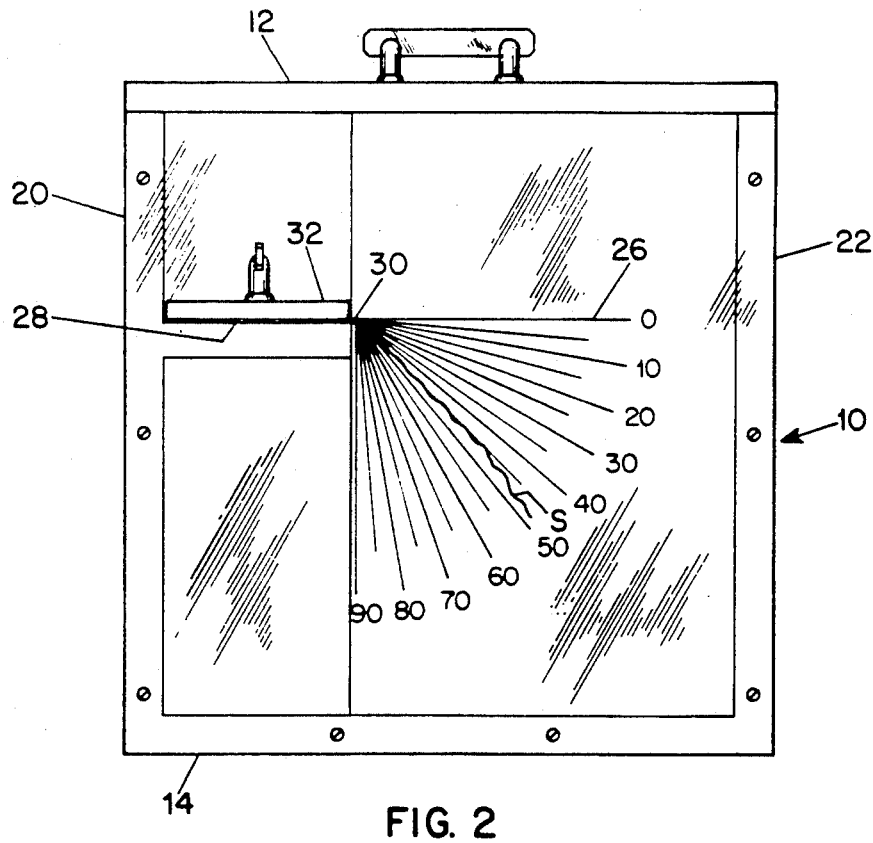
FIG. 2 is a front elevational view of the embodiment.

The embodiment comprises a box 10 having a top wall 12, a bottom wall 14, a front wall 16, a rear wall 18 and left and right side walls 20 and 22 that define a closed interior space that is free of air currents. All of the walls are flat and rectangular, which simplifies the fabrication. Except for the top and front walls all of the walls are made of plywood or particle board, again for reasons of ease of fabrication and assembly. The top wall is hinged to the rear wall so that it can be opened to permit access to the inside of the box. A plate glass mirror 24 is fastened to the inside surface of the rear wall, plate glass being preferred to enhance the parallax between indicia 26 marked on the inside face and the image of the indicia reflected by the reflective layer on the rear face. The front wall is transparent to enable the space and the indicia on the mirror to be viewed from outside the box. The top wall is transparent to permit ambient light to illuminate the inside of the box. The transparent walls are preferably fabricated from acrylic sheet.

A shelf 28, which may be made of wood, is attached to the left side wall 20 and the rear wall 18. The shelf has a planar top surface bounded by a straight edge 30 that is aligned substantially perpendicularly to the front wall 16. The shelf 28 is adapted to support a portion of a fabric sample S with the remainder of the sample draping freely from the straight edge. A plate 32 is provided for holding the portion of the sample S flat and stationary on the shelf. The indicia 26 marked on the inside surface of the mirror indicate the amount of drape of the portion of the fabric draping from the edge of the shelf. The amount of the drape is a function of the stiffness of the fabric sample. The indicia consists of straight lines extending radially in diverse directions with respect to a point where a line defined by the straight edge 30 of the shelf 28 intersects the inside surface of the rear wall 18 and different characters, such as a number representing the angle of slope with respect to the horizontal of the line corresponding to the character, for distinctly identifying each line.

For use, the tester is placed on a table or bench or mounted on legs with the shelf horizontal. The top is opened, and a sample S of predetermined size and shape is placed on the shelf. One edge of the sample is positioned at the juncture between the shelf and the side wall of the box. A side edge of the sample is lined up with a line marked on the shelf to ensure that the sample is not cocked with respect to the edge of the shelf. The plate 3 is placed on top of the portion of the sample that rests on the shelf to hold that portion flat and stationary. The top of the box is closed. The operator then looks through the front wall of the box and observes where the free end of the portion of the sample that drapes from the shelf is with respect to the indicia lines and records the number of the line where the end of the sample resides. In making the observation, the operator positions his or her eyes such that the sample is viewed from a vantage point where the indicia line marked on the surface of the mirror indicating the location of the draped end of the sample is aligned with the image of that line reflected by the mirror, thereby eliminating parallax and improving the accuracy of the observation.

I claim:

1. Apparatus for testing the stiffness of fabrics comprising a box having top, bottom, front, rear and left and right side walls defining a space that is free of air currents, the top wall being movable to permit access to the space, the rear wall including a mirror having a planar inside surface and a planar rear surface parallel to and spaced apart from the inside surface and having a reflective layer on the rear surface, and the front wall being planar and parallel to the inside surface of the rear wall and being transparent to enable the space and the inside of the rear wall to be viewed from outside the box, a shelf mounted within the space, the shelf having a planar top surface bounded by a straight edge that is aligned substantially perpendicularly to the front wall and being adapted to support a portion of a fabric sample with the remainder of the sample draping freely from said straight edge, a plate adapted to be placed on said portion of the sample so as to hold it flat and stationary on the shelf, and indicia marked on the inside surface of the mirror to indicate the amount of drape of said remainder of the fabric draping from the edge of the shelf, the indicia being reflected by the reflective layer so that the indicia and the reflection of the indicia may be aligned by a viewer to eliminate parallax.

2. Apparatus according to claim 1 wherein the top wall of the box is transparent to admit light to facilitate viewing the sample and the indicia.

3. Apparatus according to claim 1 wherein the indicia consists of straight lines extending radially in diverse directions with respect to a point where a line defined by the straight edge of the shelf intersects the inside surface of the rear wall and different characters for distinctly identifying each line.

* * * * *